United States Patent
Summer et al.

(10) Patent No.: US 9,464,267 B2
(45) Date of Patent: *Oct. 11, 2016

(54) STAGED BACTERIOPHAGE REMEDIATION OF TARGET BACTERIA

(71) Applicant: Dow Global Technologies LLC, Midland, MI (US)

(72) Inventors: Elizabeth J. Summer, College Station, TX (US); Mei Liu, College Station, TX (US); Neil S. Summer, College Station, TX (US); Douglas Baldwin, College Station, TX (US)

(73) Assignee: Dow Global Technologies LLC, Midland, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/056,808

(22) Filed: Oct. 17, 2013

(65) Prior Publication Data
US 2014/0273159 A1    Sep. 18, 2014

Related U.S. Application Data

(60) Provisional application No. 61/783,415, filed on Mar. 14, 2013.

(51) Int. Cl.
*C12N 1/06* (2006.01)
*C12N 7/02* (2006.01)

(52) U.S. Cl.
CPC .. *C12N 1/06* (2013.01); *C12N 7/02* (2013.01)

(58) Field of Classification Search
None
See application file for complete search history.

(56) References Cited

U.S. PATENT DOCUMENTS

| | | |
|---|---|---|
| 3,105,014 A | 9/1963 | Harrison |
| 4,442,895 A | 4/1984 | Lagus et al. |
| 4,778,653 A | 10/1988 | Kamimura et al. |
| 5,160,433 A | 11/1992 | Nielson et al. |
| 5,441,873 A | 8/1995 | Knight et al. |
| 6,699,701 B1 | 3/2004 | Sulakvelidze et al. |
| 6,926,833 B2 | 8/2005 | Van Reis et al. |
| 7,256,160 B2 | 8/2007 | Crews et al. |
| 7,674,467 B2 | 3/2010 | Sulakvelidze |
| 7,882,895 B2 | 2/2011 | Kabishcher et al. |
| 8,168,419 B2 | 5/2012 | Baldwin et al. |
| 8,241,498 B2 | 8/2012 | Summer et al. |
| 8,241,499 B2 | 8/2012 | Liu et al. |
| 8,252,519 B2 | 8/2012 | Baldwin et al. |
| 8,252,576 B2 | 8/2012 | Campbell et al. |
| 8,585,899 B2 | 11/2013 | Baldwin et al. |
| 2006/0094076 A1 | 5/2006 | Stave et al. |
| 2008/0213752 A1 | 9/2008 | Stave et al. |
| 2009/0104157 A1 | 4/2009 | Solomon et al. |
| 2009/0180992 A1 | 7/2009 | Summer et al. |
| 2009/0246336 A1 | 10/2009 | Burnett et al. |
| 2011/0053144 A1 | 3/2011 | Garcia Aljaro et al. |
| 2011/0281329 A1 | 11/2011 | Lenherr et al. |
| 2013/0149753 A1 | 6/2013 | Summer et al. |
| 2013/0149759 A1 | 6/2013 | Summer et al. |
| 2014/0061123 A1 | 3/2014 | Summer et al. |
| 2014/0102975 A1* | 4/2014 | Summer et al. .............. 210/601 |

FOREIGN PATENT DOCUMENTS

| | | |
|---|---|---|
| WO | WO 02/40642 | 5/2002 |
| WO | WO-2006/050193 | 5/2006 |
| WO | WO 2008/078978 | 7/2008 |

OTHER PUBLICATIONS

Office Action dated Mar. 17, 2016 in related U.S. Appl. No. 14/060,297, filed Oct. 22, 2013.
Office Action dated May 19, 2015 in related U.S. Appl. No. 14/060,297, filed Oct. 22, 2013.
Applicant's Response dated Oct. 19, 2015 to the Office Action in related U.S. Appl. No. 14/060,297, filed Oct. 22, 2013.
Office Action dated Jun. 17, 2013 in related U.S. Appl. No. 13/465,700, filed May 7, 2012.
Applicant's Response dated Jul. 16, 2013 to the Office Action in related U.S. Appl. No. 13/465,700, filed May 7, 2012.
Office Action dated Nov. 5, 2013 in related U.S. Appl. No. 13/465,700, filed May 7, 2012.
Applicant's Response dated Dec. 18, 2013 to the Office Action in related U.S. Appl. No. 13/465,700, filed May 7, 2012.
Office Action dated Sep. 23, 2014 in related U.S. Appl. No. 13/465,700, filed May 7, 2012.
Applicant's Response dated Apr. 3, 2015 to the Office Action in related U.S. Appl. No. 13/465,700, filed May 7, 2012.
Office Action dated Aug. 5, 2015 in related U.S. Appl. No. 13/465,700, filed May 7, 2012.
Applicant's Response dated Nov. 5, 2015 to the Office Action in related U.S. Appl. No. 13/465,700, filed May 7, 2012.
Abedon, S. et al. Experimental Examination of Bacteriophage Latent-Period Evolution as a Response to Bacterial Availability, Applied and Environmental Microbiology, Dec. 2003, 69 (12): 7499-7506.
Lu, T.K. et al., Dispersing biofilms with engineered enzymatic bacteriophage, PNAS, Jul. 2007, 104 (27): 11197-11202.
Zacheous, O.M. et al., Soft deposits, the key site for microbial growth in drinking water distribution networks, Water Research, May 2001, 35 (7): 1757-1765.
Scholtens, et al., ("Phage Typing of *Salmonella typhi* in the Netherlands", from the Rijks Instituut voor de Volksgezondheid, Utrecht; Jun. 6, 1950).

(Continued)

*Primary Examiner* — Nicole Kinsey White
(74) *Attorney, Agent, or Firm* — Tifani M. Edwards

(57) ABSTRACT

A process for remediation of target bacteria, particularly sulfur reducing bacteria (SRB), in waters ("target water") having a multiplicity and diverse host target bacteria by employing serial or staged bacteria culturing and lysing of dominant bacteria. Remediation of sulfur reducing bacteria (SRB) is effected by application of a series of bacteriophage isolated from the staged culturing and bacteriophage lysing of successive aliquots of waters containing a multiplicity of SRB.

13 Claims, 1 Drawing Sheet

(56) References Cited

OTHER PUBLICATIONS

Greenberg, et al., ("Tracing Typhoid Carriers by Means of Sewage", presented at the 1957 annual meeting, California Sewage and Industrial Wastes Assn.; San Diego, CA.; May 1-4, 1957).

Derwent Translation of Araki et al. (JP 02099196) of Apr. 1990.

Sakaguchi, et al., (Control of Microbiofouling Using Bacteriophage 2. Detection of Phages and Fundamental Study of their Lytic Effect on Fouling Bacteria (Abstract Only), De. 1989.

Lee, et al., (Molecular analysis of a mixed-species biofilm on carbon steel. Abstracts of the General Meeting of the American Society for Microbiology. 2003; vol. 103:Q-156.

Jiang, S.C. et al., Significance of lysogeny in the marine environment: studies with isolates and a model of lysogenic phage production, Microbial Ecology, May 1998, 35 (3): 235-243.

McNair, et al., (Predicting Phage Preferences: Lytic vs. Lysogenic Lifestyle from Genomes:. 2013 from the San Diego State University).

Office Action dated May 19, 2015 in related U.S. Appl. No. 14/133,115, filed Dec. 18, 2013.

Applicant's Response dated Oct. 19, 2015 in related U.S. Appl. No. 14/133,115, filed Dec. 18, 2013.

Office Action dated Jan. 29, 2016 in related U.S. Appl. No. 14/133,115, filed Dec. 18, 2013.

* cited by examiner

STAGED BACTERIOPHAGE REMEDIATION OF TARGET BACTERIA

RELATIONSHIP TO OTHER APPLICATIONS

This application claims benefit of Application Ser. No. 61/783,415 filed Mar. 14, 2013; the disclosure and figures of which are incorporated herein by reference in their entirety for all purposes.

BACKGROUND

1. Field of Invention

Remediation of target bacteria occurs by application of a mixture of or serial application of bacteriophage isolated by staged culturing and bacteriophage lysing of bacteria in waters containing a multiplicity of target bacteria. The process is particularily effective for sulfur reducing (SRB) and acid producing bacteria (APB).

2. Background

Microbial fouling affects the entire infrastructure of the oil and gas industry, from production wellheads, throughout transmission pipelines, and the refinery. In particular, sulfate-reducing bacteria (SRB) sour and devalue the petroleum product in reservoirs through the evolution of $H_2S$ (hydrogen sulfide) gas. Because H2S was both flammable and a potent neurotoxin, elevated levels were responsible for increased overall risks and costs during exploration and production. Chemical biocides were widely applied to combat bacterial related problems. Biocide treatment results in suppression, rather than elimination, of the problem organisms and has the major drawback of being harmful to humans and the environment. Investigation into new approaches of controlling microbial population in the petroleum industry is prudent.

A relatively new method for controlling SRB is by use of bacteriophage, or phage. Phages are natural, bacteriolytic, viral predators of bacteria. Phages are already being used commercially to control bacteria on cattle and food crops. Phage treatments are available overseas for treating human bacterial infections, particularly in chronic wounds and burns. Regulatory hurdles have prohibited medical applications in the US. However, by analogy it might be possible to develop phage based products to control "bacterial infections" of the oilfield and it is conceivable that a mixture of oilfield SRB-specific phage could be injected at the head of a pipeline or into a reservoir to control SRB associated corrosion and souring.

However, in some trials of oil and gas field waters containing a plethora of SRB varieties, treatment with phage has been found short lived, with bacterial levels being reduced for a short period of time and then recovering. Recovery of total bacterial levels has been found to be due to the appearance of resistant varieties of the original host strain as well as due to the proliferation of minority bacterial strain following the elimination of the dominant bacterial type. Resistance can be due to any number of mechanisms, including the appearance of lysogens or the selection for novel natural genetic variants.

DESCRIPTION OF FIGURES

The accompanying Figures illustrate specific results from embodiments of the invention and, together with the general description of the invention given above, and the detailed description of the specific embodiments, serve to explain the principles of the invention.

DETAILED DESCRIPTION

Figure 1:
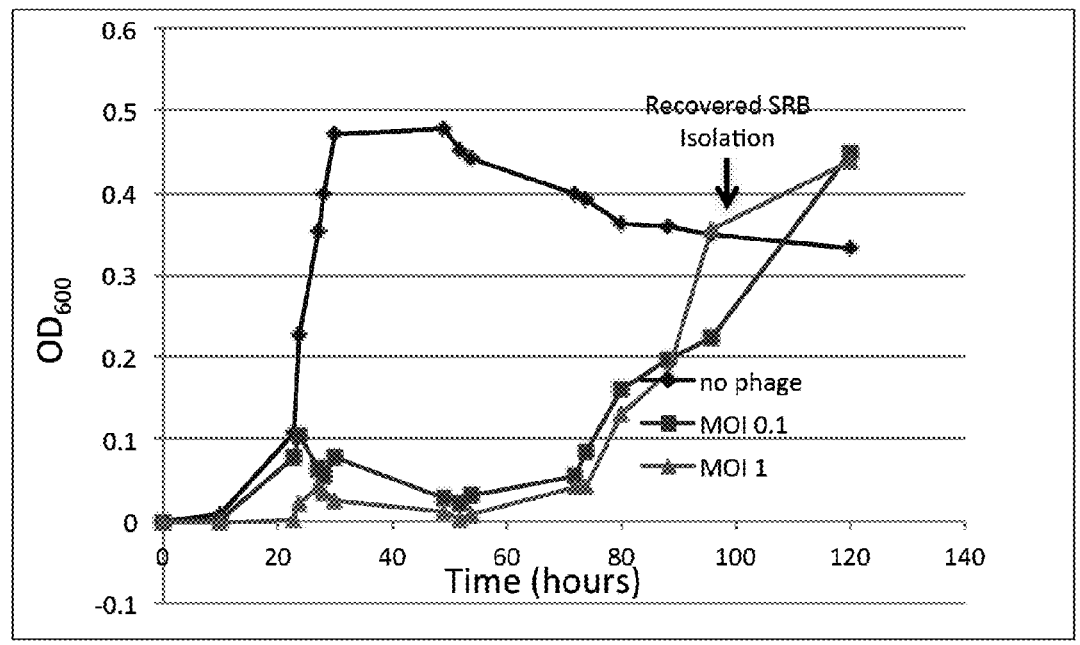
FIG. 1 is a graphical plot of a growth curve of illustrative bacteria treated with virulent phage.

In a broad aspect, the present invention is a process for remediation of target bacteria particularly sulfur reducing bacteria (SRB) in waters ("target water") of a multiplicity and diverse host target by employing serial or staged bacteria culturing and lysing of dominant bacteria. Remediation of sulfur reducing bacteria (SRB) is effected by application of a series of bacteriophage isolated from the staged culturing and bacteriophage lysing of successive aliquots of waters containing a multiplicity of SRB.

Control of a broad range of target bacteria is achieved by application of virulent bacteriophage(s) obtained by culturing dominant bacteria in a mix of bacteria by:

culturing a dominant group of bacteria in a mixed bacteria solution, isolating virulent phage(s) for the dominant bacteria, lysing dominant bacteria from a sample of the mixed bacteria solution to remove the dominant bacteria from the mix;

culturing the next dominant strain from the solution with the dominant strain lysed, isolating a virulent phage for the next dominant bacteria, lysing it to remove the next dominant bacteria; and continuing the sequence to provide a set of bacteriophage that will lyse the dominant and sub-dominant bacteria; and applying an effective amount of the isolated phage(s) to a target solution of mixed bacteria.

This will provide a basis for production, as disclosed herein, of phage that will lyse dominant and sub-dominant bacteria in a mixed community of bacteria.

These phage can then be mixed and applied to lyse target dominant and sub-dominant bacteria. The so isolated bacteriophage for dominant and sub-dominant bacteria can be applied sequentially to lyse first the dominant bacteria(s) and subsequently the series of sub-dominant bacteria(s) that proliferate when the next dominant bacteria is reduced or removed. The staging can be applied in response to tests to determine when the sub-dominant bacteria begin to proliferate in the mixture or simply on a timed schedule. For example, phage virulent for the dominant bacteria is first applied to a mixture of target bacteria and when growth of sub-dominant bacteria are detected phage virulent for the first sub-dominant bacteria are applied and the sequence continued for all sub-dominant bacteriophage isolated.

In another embodiment, where temperate phage are produced, temperate phage are isolated by assaying the culture supernatant for the steady-state phage produced, or prophage are induced by application of a stressing agent such as a chemical (for example, mitomycin C) or ultraviolet radiation. Temperate phage may be used directly or a virulent isolate of the temperate phage may be first isolated prior to use in SRB control.

Thus, in this embodiment, phage is isolated for control of a diverse mix of target bacteria by:

culturing a dominant group of bacteria from a diverse mixture of target bacteria, isolating virulent phage active against the dominant bacteria;

isolation of temperate phages from these bacterial strains from the culture supernatant; stressing the temperate bacteria to convert into virulent phages for use in phage preparations;

continuing the sequence until a collection of bacteriophage is assembled that will effect significant and lasting of problematic bacteria; and Stressing bacteria containing temperate (or lysogenic) phage to cause temperate phage to lyse and produce phage that will lyse other bacteria is described in patent Application to Illison, WO02/40642. Jun. 23, 2002. Illson discloses, at page 2, "Stressing bacteria so that they lyse or rupture and die producing viruses called bacteriophages which then kill other bacteria is a very efficient way of killing bacteria without the large scale use of biocidal chemicals which can be damaging to the environment. The bacteriophages produced by the lysing bacteria are specific to other bacteria of the same type.

The bacteria can be stressed by any suitable method such as the application of an appropriate amount of ultra-violet light, heat, antibiotics or chemicals that are toxic to the bacteria. The amount of ultra-violet light, heat, toxic or stress inducing chemicals or antibiotics to which the bacteria are exposed is predetermined in experiments to ensure that it stresses a bacterium but does not immediately kill it before it produces bacteriophages which can then be used to kill other bacteria." This disclosure is incorporated herein and made a part of the disclosure of this invention.

Target bacteria will generally be sulfate reducing bacteria (SRB), or acid producing bacteria.

The process is particularly suitable for remediation of *Desulfovibrio* species bacteria.

Culturing of SRB from mixed bacteria containing waters, isolating phage virulent for cultured bacteria and reproducing the phage and assembly of phage panel and cocktail is well described in U.S. Pat. No. 8,241,498 issued Aug. 14, 2012; U.S. Pat. No. 8,168,419 issued May 1, 2012; U.S. Pat. No. 8,252,576 issued Aug. 28, 2012, U.S. Pat. No. 8,252,519 issued Aug. 28, 2012 and Published application US 2009/0180992 published Jul. 16, 2009, the relevant disclosures and figures of which are incorporated herein by reference.

Phage once isolated can be proliferated to production level for use by means known in the art. A particularly suitable method is disclosed in U.S. Pat. No. 8,168,419 issued May 1, 2012 the disclosure of which is incorporated herein by reference.

Two traits of significance in culturing bacteria are the bacterial growth rate as well as the bacterial concentration. Experiments were conducted in batch cultures. Batch cultures are prepared by inoculating liquid media and allowing the culture to grow without addition of fresh media or removal of spent media. Batch cultures undergo "single step growth kinetics", such that the culture progresses through an initial period of slow growth known as "lag phase", followed by a period of rapid, logarithmic growth known as "log phase", and finally, the culture enters "stationary phase" during which the growth rate slows or even stops as nutrients in the media were depleted and metabolic wastes build up and poison the culture. Log phase is further divided into early, middle, and late log phase. Bacteria with slower doubling times may take days or weeks to accumulate to a high enough level to perform each step of the phage isolation and purification. The time required to conduct efficacy studies also increases as growth rate decreases. The second growth characteristic of each strain that needed to be evaluated in order to conduct phage efficacy trials was the typical concentration of cells, in terms of active cells/ml during the different stages of growth.

The bacterial cells/ml value is needed in order to estimate the multiplicity of infection (MOI) during the efficacy trials. MOI is the ratio of phage particles to bacterial cells added to the experiment. Experiments are typically conducted at MOI of 0.01, 0.1, 1, 10, and 100.

The traditional method used to monitor bacterial growth is by measuring changes in light absorption at A600 using a spectrophotometer and correlating this value to the number of colony forming units (cfu) per ml. Several issues prevented this from being accomplished in the traditional method. First, when made with iron sulfate, standard MPB media contains precipitates that interfere with spectrophotometric readings. Therefore, all experiments in which A600 are measured were conducted using media in which the iron sulfate is omitted. Second, the SRB do not form colony-forming units quantitatively because growth is less robust on solid media. To accommodate this limitation, instead of colony forming units, the cell concentration at different points in the experiments was determined by MPN or serial dilution analysis The first step in isolating phages active against the SRB was to evaluate the capacity of the different SRB to form confluent lawns in top agar. This step is required to visualize phage plaques following standard procedures. Lawns prepared using *D. longus* and *D. alaskensis* develop in over 48 hours. Lawns prepared using *D. desulfuricans* and *D. gabonensis* lawns were too thin for assaying phage on MPB plates.

Efforts to improve lawn characteristics by increasing the amount of bacteria did not improve lawn characteristics. Phage isolations were performed using the enrichment method (Summer et al., 2009). Phage enrichments were set up with purified SRB and ATCC strains using various rinsates, including 3 samples provided by Shell, as well as 22 additional samples (Table 3 and data not shown). Enrichments were set up in 50 ml volumes, containing 25 ml fresh MPB, 25 ml environmental rinsate, and 0.2 ml of log phase host cells. The enrichments were incubated at room temperature and sampled for the presence of phage at 1, 3, 7 and 14 days. At each time point, phages were screened by spotting filter-purified enrichment onto lawns of each host.

In samples where phages were detected, the highest concentrations of phage were observed 3 days into the enrichment, after which titers begins to drop. Phage present in positive enrichments was processed by plaque purification. To accomplish this, phage were diluted and plated in overlays. Well-separated plaques were excised and phage eluted, forming a pickate. The pickate was then diluted and plated in an overlay lawn and the pickate process repeated. Finally, the phage stock was amplified in a stepwise fashion, first by making a 5 ml lysate from a single plate and then generating a 50 ml phage stock. The SRB phage titers were typically found to be quite low, typically between 106 to 108 pfu/ml. In contrast, a typical *E. coli* phage stock will have a titer of approximately 109 pfu/ml.

Since bacteria growth and survival (and dominance) are influenced by indigenous conditions, such as temperature, salinity and pH of the water and the like, it is preferred that culturing as described above is conducted under conditions that simulate those where use of the produced phage panel/cocktail will be made. Simulating such conditions present some special problems in culturing and testing of isolated virulent phage.

The invention is generally described herein in relation to SRB in oil and gas well water applications. But the invention is equally applicable to other SRB containing waters such as cooling tower water, pulp and paper mill waters, and the like such as waters described in U.S. Pat. No. 8,241,498, Aug. 14, 2012, the relevant disclosures of which are incorporated herein by reference. Culturing at approximated anaerobic treatment conditions and elevated temperature.

The subsurface environment varies from ambient temperature and pressure to extremely elevated temperatures and pressures considered non-permissive for life. Organisms that require elevated temperatures and pressure require special manipulation. High temperature conditions complicate almost every step in the phage isolation and manipulation process. For example, standard phage agar solidifies at around 50° C., however, bacteria such as *Archaeoglobus* is likely to require at least 70° C. for regular growth. Therefore, visualizing plaques in culture overlays require the use of high-temperature solidifying agents, for example the use of gellan gum based solidifying agents, sold under the trade name of Phytagel (Sigma) (Wirth et al., 2011).

EXPERIMENTAL EVIDENCE

In sample waters of test oil well site (produced water) *Desulfovibrio* species were found to be present at all sites at well site and the only SRB at most sites. *Desulfovibrio* species from the site were found to be closely related to cultured *Desulfovibrio* species. Examples of different SRB established in mixed cultures from the site included strains highly similar to the following database entries: *D. vietnamensis* (T) type, strain: G3 100 ID95-371; (X93994), *D. desulfuricans desulfuricans* Essex 6, ATCC29577 (AF192153), *D. alaskensis* (T) type strain: Al1=NCIMB 13491, (Y11984) as well as *D. dechloracetivorans* Mic23c06 (AB546251) (Magot et al., 1992; Tardy-Jacquenod et al., 1996; Feio et al., 1998; Motamedi and Pedersen, 1998; Sun et al., 2000; Allen et al., 2008).

Mixed cultures with combinations of the ATCC strains as well as de novo produced water SRB isolates were established. Phage were isolated that exhibited activity against each of these strains. Experiments were conducted using these bacterial hosts as either pure or mixed culture treated with single phages.

When phage active against only the most abundant member of a mixed bacterial population were applied to the mixed culture, bacterial levels were significantly suppressed for several days (FIG. 1). However, additional incubation time allowed for the bacterial levels to recover. FIG. 1 describes sequential phage efficacy trials and isolation of phage that overcome culture recovery. It is a growth curve of host Dala14563 either alone (no phage, diamonds) or treated at time zero with phage phiDalaCJ1 at MOI of 0.1 (box), or 1 (triangle). At the indicated time point, the SRB growing in the MOI=1 sample was isolated. Sequence analysis indicated that the recovered host is a resistant derivative of the input host.

Figure 2:
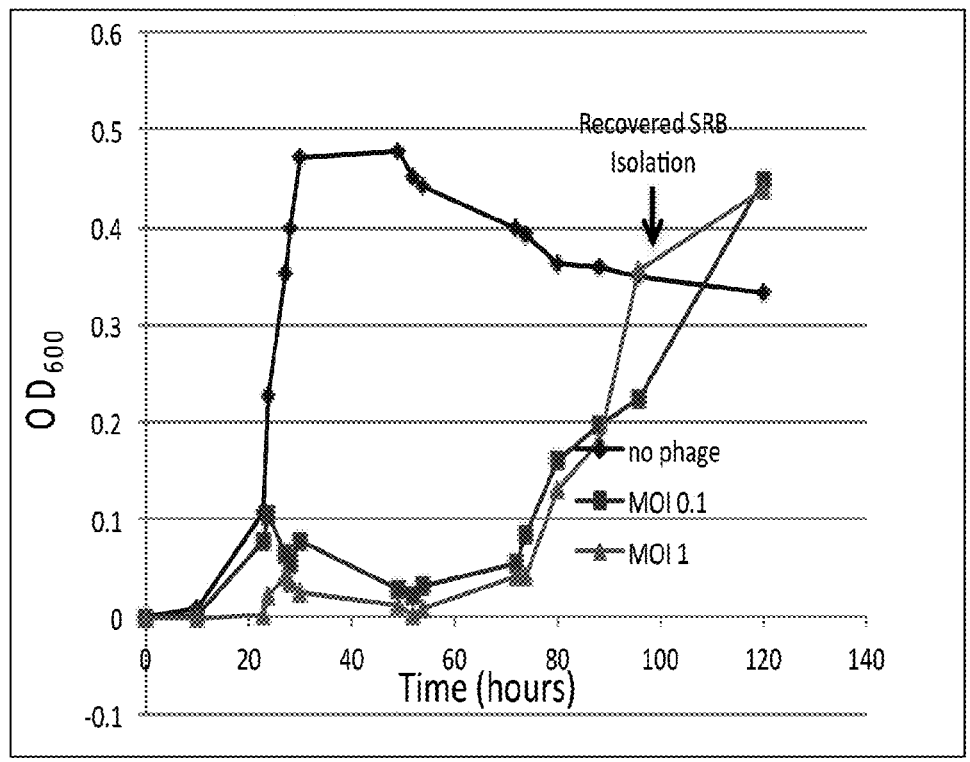
FIG. 2 is a graphical plot of a growth curve of another illustrative bacteria treated with virulent phage.

Two mechanisms were found to be responsible for the recovery. In some cases, phage resistant representatives of the dominant bacterial strain applied to the experiment arose and proliferated (FIG. 2). FIG. 2 is a growth curve of mixed hosts DalaP4 and DalaP42, inoculated at a >1000:1 ratio, either alone (no phage, green diamond) or treated at time zero with phage phiDalaP4 at MOI of 0.1 (red box), or 1 (blue triangle). At the indicated time point, the SRB growing in the MOI=1 sample was isolated. Sequence analysis indicated that the recovered host is DalaP42, the minority inoculum.

In other cases, the minority organism in the inoculation proliferated and became the numerically dominant organism in the culture (FIG. 2). In both cases, phage capable of killing the bacteria in the recovered population was isolated. This clearly demonstrates that phages can be isolated capable of killing the bacteria that arise following treatment with a partially effective phage preparation.

In the foregoing specification, the invention has been described with reference to specific embodiments thereof. It will, however, be evident that various modifications and changes can be made within the spirit and scope of the invention as will be apparent to those skilled in the art from this description and by practice of the invention without departing from the broader spirit and scope of the invention as set forth in the appended claims. The scope of the invention is not intended to be limited to the particular forms disclosed and the invention covers all modifications, equivalents, and alternatives falling within the spirit and scope of the invention as defined by the claims. The specification is, accordingly, to be regarded in an illustrative rather than a restrictive sense. Therefore, the scope of the invention should be limited only by the appended claims.

The invention claimed is:

1. A process for control of multiple target bacteria in a water source comprising the following sequential steps:
   (a) culturing a first dominant bacteria in a first mixed bacteria solution obtained from the water source, said first mixed bacteria solution containing dominant bacteria and sub-dominant bacteria, isolating a virulent phage for the first dominant bacteria, and lysing the first dominant bacteria from the first mixed bacteria solution to remove the first dominant bacteria from the mixed solution, thereby generating a second mixed bacteria solution lacking the first dominant bacteria;
   (b) culturing the next dominant bacteria from the second mixed bacteria solution lacking the first dominant bacteria; isolating a virulent phage for the next dominant bacteria and lysing the next dominant bacteria from the second mixed bacterial solution to remove the next dominant bacteria, thereby generating a subsequent mixed bacterial solution lacking both the first and next dominant bacteria;
   (c) performing the culturing, isolating, and lysing steps on each subsequent mixed bacterial solution to provide a set of bacteriophage that will lyse the first dominant bacteria and multiple subdominant bacteria in the first, second and subsequent mixed bacteria solutions; and
   (d) applying an effective amount of the bacteriophage of said set either as a mixture or sequentially to the water source.

2. The process of claim 1 wherein the first dominant and each sequentially subdominant bacteria in the first, second and subsequent mixed bacteria solutions are sulfate reducing bacteria.

3. The process of claim 1 wherein the dominant bacteria is a temperate bacteria that is stressed to produce virulent phages.

4. The process of claim 1 wherein target bacteria are selected from the group consisting of *Proteobacteria, Desulfobacterales, Desulfovibrionales, Syntrophobacterales, Thiobacilli, T. thiooxidans, T. denitrificans, Gallionella* and *Siderophacus*.

5. The process of claim 1, wherein the culturing of bacteria in the sequential steps is conducted using conditions that substantially approximate the conditions where the bacteriophages will be used against target bacteria or the conditions under which the bacteriophage were isolated from the mixed solution.

6. The process of claim 5, wherein the culturing conditions comprise the parameters of temperature, oxygen level and salinity.

7. The process of claim 1 wherein at least three sequential culturing, isolating and lysing steps are conducted to produce phage virulent for a first dominant bacteria, a sequentially sub-dominant bacteria, and a further sequentially sub-sub-dominant bacteria detected in the water source.

8. The process of claim 1, wherein the water source is selected from the group consisting of water from oil or gas operations, cooling water tower water, and pulp and paper operations process and waste waters.

9. The process of claim 1, wherein step (d) further comprises applying the phage virulent for the first dominant bacteria to a mixture of target bacteria in the water source, and applying phage virulent for each subsequent sub-dominant bacteria after growth of each said sub-dominant bacteria in the water source is sequentially detected.

10. A process for control of multiple target bacteria in a water source comprising:
(a) culturing a dominant bacteria from a first mixture of target bacteria obtained from the water source, and isolating a virulent phage for the dominant bacteria;
(b) isolating a temperate bacteria present in the first mixture and stressing the temperate bacteria to produce an additional virulent phage that can lyse the temperate bacteria;
(c) repeating steps (a) and (b) and assembling a set of virulent phage that can lyse multiple dominant and temperate bacteria in the water source; and
(d) applying an effective amount of the virulent phage either as an assembled set or sequentially to a water source containing a mixture of target bacteria the same as those found in said first mixture.

11. The process of claim 10 wherein the temperate bacteria in the first mixture are stressed by application of an appropriate amount of ultra-violet light, heat, antibiotics or chemicals that are toxic to the bacteria.

12. The process of claim 10 wherein the dominant bacteria in the first mixture are sulfate reducing bacteria.

13. The process of claim 10 wherein at least three repetitions of steps (a) and (b) are conducted to produce a set of virulent phage that includes a phage virulent for a dominant bacteria, a phage virulent for a sub-dominant bacteria and a phage virulent for a sub-sub-dominant bacteria in the water source.

* * * * *